(12) United States Patent
Visconti et al.

(10) Patent No.: US 9,402,939 B2
(45) Date of Patent: Aug. 2, 2016

(54) DISPOSABLE SURGICAL SUCTION/IRRIGATION TRUMPET VALVE TUBE CASSETTE

(71) Applicant: Allegiance Corporation, McGaw Park, IL (US)

(72) Inventors: Peter Visconti, Gurnee, IL (US); Thomas A. Doering, Grayslake, IL (US); Kenneth W. Horton, Kildeer, IL (US); Janice B. Wells, Davie, FL (US); Robert W. Thomas, New Boston, NH (US); James Hansen, New Boston, NH (US); Gary P. Schroeder, Londonderry, NH (US); Ashvin Desai, San Jose, CA (US)

(73) Assignee: Allegiance Corporation, Waukegan, IL (US)

( * ) Notice: Subject to any disclaimer, the term of this patent is extended or adjusted under 35 U.S.C. 154(b) by 0 days.

(21) Appl. No.: 14/320,891

(22) Filed: Jul. 1, 2014

(65) Prior Publication Data

US 2015/0073346 A1 Mar. 12, 2015

Related U.S. Application Data (60) Division of application No. 11/702,963, filed on Feb. 6, 2007, now Pat. No. 8,795,232, which is a division of application No. 10/759,360, filed on Jan. 16, 2004, now Pat. No. 7,776,014, which is a division of application No. 09/574,164, filed on May 18, 2000, now abandoned, which is a continuation-in-part of application No. 09/492,964, filed on Jan. 28, 2000, now Pat. No. 6,375,653, which is a continuation of application No. 09/015,299, filed on Jan. 29, 1998, now Pat. No. 6,027,502.

(51) Int. Cl.
| | | |
|---|---|---|
| *A61M 37/00* | (2006.01) | |
| *A61M 1/00* | (2006.01) | |
| *A61B 17/00* | (2006.01) | |
| *A61M 3/02* | (2006.01) | |
| *A61B 18/14* | (2006.01) | |
| *A61B 18/00* | (2006.01) | |
| *A61B 18/12* | (2006.01) | |
| *A61B 18/18* | (2006.01) | |

(52) U.S. Cl.
CPC ........ *A61M 1/0058* (2013.01); *A61B 17/00234* (2013.01); *A61B 18/1482* (2013.01); *A61M 1/0043* (2013.01); *A61M 1/0072* (2014.02); *A61M 3/0258* (2013.01); *A61B 18/14* (2013.01); *A61B 2018/00208* (2013.01); *A61B 2018/1253* (2013.01); *A61B 2018/1497* (2013.01); *A61B 2018/1861* (2013.01); *A61B 2218/002* (2013.01); *A61B 2218/007* (2013.01); *A61M 1/0031* (2013.01); *A61M 1/0064* (2013.01); *A61M 2205/12* (2013.01)

(58) Field of Classification Search
CPC ........... A61M 5/14224; A61M 5/142; A61M 5/14244
USPC ................... 604/131, 890.1–892.1, 132, 133
See application file for complete search history.

(56) References Cited

U.S. PATENT DOCUMENTS

4,808,167 A * 2/1989 Mann .................. A61M 5/1413
128/DIG. 12

*Primary Examiner* — Phillip Gray
(74) *Attorney, Agent, or Firm* — Jacob R Lenzke (57) ABSTRACT

The present invention provides a disposable trumpet valve tube cassette assembly, as well as, a surgical irrigation instrument that includes a probe assembly, a pump, a removable pump cartridge, and a socket. The probe assembly provides passage of fluids for irrigating the body interior and for evacuating matter from the body interior. The pump provides for pumping irrigation fluid through the probe assembly into the body interior. A pump cartridge defines a pumping chamber. Electronic control circuitry includes an electronics controller and a trumpet valve switch interface. The electronics controller includes a pulse generator that generates pulses, the duty cycle of the pulses controlling the speed of the motor. The trumpet valve switch interface is in electronic connection to a switch, the interface providing a signal to the controller.

19 Claims, 8 Drawing Sheets

DISPOSABLE SURGICAL SUCTION/IRRIGATION TRUMPET VALVE TUBE CASSETTE

CROSS-REFERENCE TO RELATED APPLICATIONS

This application is a Divisional of U.S. patent application Ser. No. 11/702,963 filed on 6 Feb. 2007, issued as U.S. Pat. No. 8,795,232 on 5 Aug. 2014, which is a divisional of U.S. patent application Ser. No. 10/759,360 filed on 16 Jan. 2004, issued as U.S. Pat. No. 7,776,014 on 17 Aug. 2010, which was a Divisional of U.S. patent application Ser. No. 09/574,164 filed on 18 May 2000, (now abandoned) which was a continuation-in-part of U.S. patent application Ser. No. 09/492,964 filed on 28 Jan. 2000, issued as U.S. Pat. No. 6,375,653 on 23 Apr. 2002, which was a continuation of U.S. patent application Ser. No. 09/015,299 filed on 29 Jan. 1998, issued as U.S. Pat. No. 6,027,502 on 22 Feb. 2000.

FIELD OF THE INVENTION

The present invention relates to manually operated valve and probe systems for controlling the flow of irrigation and aspiration fluids to and from surgical sites.

BACKGROUND OF THE INVENTION

Laparoscopic and endoscopic surgical instruments are used to perform surgery without the need to make large incisions. These procedures are generally less invasive than conventional surgery. Surgical instruments useful in these procedures generally include a hollow probe inserted into the body, through which various scopes and other instruments may be inserted. Such instruments may include, for example, endoscopes, laparoscopes, clip appliers, microscissors, forceps, optical fibers connected to laser sources for hemostatic cutting or coagulation, electrode sets for electrocautery, as well as, suction and irrigation lines.

In addition, in such minimally invasive surgery it is often desired to irrigate an operative site with a sterile solution and then to withdraw or aspirate fluids from the surgical site under suction. The aspirated fluids can include, not only the irrigation solution, but also blood and other body fluids, tissue and fragments. Such irrigation of an operative environment poses two significant design hurdles. First, the fluid that is use to irrigate the operative site must be maintained as a sterile fluid. Second, the irrigation of an operative site requires pumping a large amount of liquid (up to three liters per minute) in a medical environment.

This irrigation and aspiration is typically achieved by use of an externally operated valve device and an elongated probe that is manipulated by the surgeon to control flows into and out of the operative site. These are referred to as to as "trumpet valves" because of the similarity of their look and feel to a trumpet.

The trumpet valves include key members on top of two adjacent and parallel valve barrels that can be selectively depressed by the surgeon against a compression spring. Depression of one key transmits irrigation fluid through the valve assembly and out through the endoscopic probe member to irrigate the surgical site. Depression of the other key opens a suction line to permit fluids to be aspirated from the surgical site through the probe and valve. Aspiration vacuum is provided to the trumpet valve by a source of vacuum.

Irrigation fluid is provided to the trumpet valve by a pump. In one prior art system the pump itself is disposable which is extremely expensive. In other prior art pump systems the pump interacts with a pump cartridge. Such diaphragm pump cartridge assemblies typically include cassette body having an inner flow chamber disposed in a one-way fluid flow passageway. The front end of the chamber is closed off by a resilient diaphragm member. The front end of the cartridge cassette is provided with mateable quick disconnect features so that the cartridge cassette may be inserted into and mated with a mateable socket defined on an electronically controlled pump.

In accordance with the typical suction irrigation system of the prior art, the electronic control of the motor is independent from the suction and irrigation actuators on the irrigation valve and probe assembly. As a result, the pump frequently remains in an on condition and thereafter, at the initiation of irrigation flow, undesirable pressure may be developed on the irrigation fluid side which is released in a jet of irrigation fluid on actuation of the probe. The jetting of fluid is undesirable because it varies unexpectedly and results in a loss of control for the surgeon. In order to turn off the pump, the surgeon must turn away from the operative site to turn the pump on or off, or must communicate commands to additional surgical personnel, which may lead to a break in the surgeon's concentration or errors in communication which are also major disadvantages.

Moreover, the probe handle assembly typical in the prior art includes flow actuator valves of a non-trumpet valve type with a lever switch which has to be manually flipped on and off by the surgeon, usually using a second hand to do so.

In addition, it is desired that the irrigation system be able to deliver, on demand, controlled but relatively large quantities of irrigation fluid in a non-distracting manner under control of the surgeon. A major problem with the diaphragm members of the prior art is that they lack the resilient properties required to refill the pumping chamber with consistency and accuracy. In an effort to increase the return performance of the diaphragm, increases in diaphragm thickness or durometer have been attempted, however, these steps place additional strain on the piston and the pump, particularly on start up, which causes stress on the pump electronics.

What would be desirable is a suction irrigation system which place direct irrigation flow under the one handed control of the surgeon. What would be further desirable is a disposable suction irrigation cassette assembly that is capable of operating with a pump in a manner which delivers consistently controlled irrigation fluid volumes, at controlled rates and pressures under the control of the surgeon. Still further, what would be desirable is an irrigation system that is able to deliver, on demand, consistent and accurate quantities of irrigation fluid in a non-distracting manner under control of the surgeon. Additionally, the irrigation system should prevent the pump from burning itself out.

SUMMARY OF THE INVENTION

The present invention provides a suction irrigation system that places direct irrigation flow under the one handed control of the surgeon. The present invention further provides a disposable suction irrigation cassette assembly that is capable of operating with a pump in a manner which delivers consistently controlled irrigation fluid volumes, at controlled rates and pressures under the control of the surgeon. The present invention provides a suction irrigation system that is able to deliver, on demand, consistent and accurate quantities of irrigation fluid in a non-distracting manner under control of the surgeon. The present invention provides control circuitry so that the pump will shut off prior to burning itself out.

To do so, the present invention provides a new and improved disposable trumpet valve tube cassette assembly, as well as, a new and improved surgical irrigation apparatus generally comprising a disposable trumpet valve tube cassette assembly and a modified and improved electronically controlled pump.

In an embodiment, the present invention includes a surgical instrument that includes a probe assembly, a pump, a removable pump cartridge, and a socket. The probe assembly provides passage of fluids for irrigating the body interior and for evacuating matter from the body interior. The pump is remotely located from the probe assembly and provides for pumping irrigation fluid from a source of the fluid through the probe assembly into the body interior. The pump includes a motor connected to a reciprocating drive for actuating a piston to drive the diaphragm. The removable pump cartridge defines a cavity, a one way fluid inlet to the cavity, a one way fluid outlet from the cavity, and a flexible diaphragm for covering the cavity. The socket defines a through hole through the socket for passage of the piston, the socket and the pump cartridge including cooperating tabs and grooves to engage the pump cartridge with the socket, with the piston positioned in operative engagement with the flexible diaphragm.

In an embodiment, the present invention includes an surgical irrigation pump for use with a cartridge cassette having a pumping chamber. The surgical irrigation pump includes a pumping actuator, a socket, and a motor. The socket is contained on the pump housing for removably receiving the cartridge cassette to establish working communications between the pumping actuator and the pumping chamber, with the motor in operative engagement with the pump actuator.

In an embodiment, the present invention includes a cartridge cassette for use with an surgical irrigation pump having a pumping actuator. The cartridge cassette includes a pumping chamber in fluid communication with a source of fluid and an irrigation conduit. A tab-receiving groove is provided in the cartridge cassette which is adapted to mate with a laterally outwardly projecting tab on the surgical irrigation pump to provide coupling of the cartridge cassette in the surgical irrigation pump to establish working communication with the pumping actuator. An upstream valve is disposed in the cartridge and in fluid communication with the source of fluid and the pumping chamber. A downstream valve disposed in the cartridge and in fluid communication with the irrigation conduit and the pumping chamber.

In an embodiment, the present invention includes an electronic control circuitry comprising an electronics controller and a trumpet valve switch interface. The electronics controller includes a pulse generator that generates pulses, the duty cycle of the pulses controlling the speed of the motor. The trumpet valve switch interface is in electronic connection to a switch, the interface providing a signal to the controller.

In an embodiment, the present invention includes a diaphragm for use in a cassette having a pump chamber and a surgical irrigation pump having a pumping actuator. The diaphragm includes an inner portion that faces the pump chamber of the cassette and an outer portion that interacts with the pumping actuator. Means are provided to follow the piston while improving the return stroke. This means can include a graduated cross-sectional thickness dimension of the diaphragm such that the thickness dimension increases from a central portion of the diaphragm to radially outward portions of the diaphragm.

DETAILED DESCRIPTION OF AN EMBODIMENT OF THE INVENTION

Figure 1:
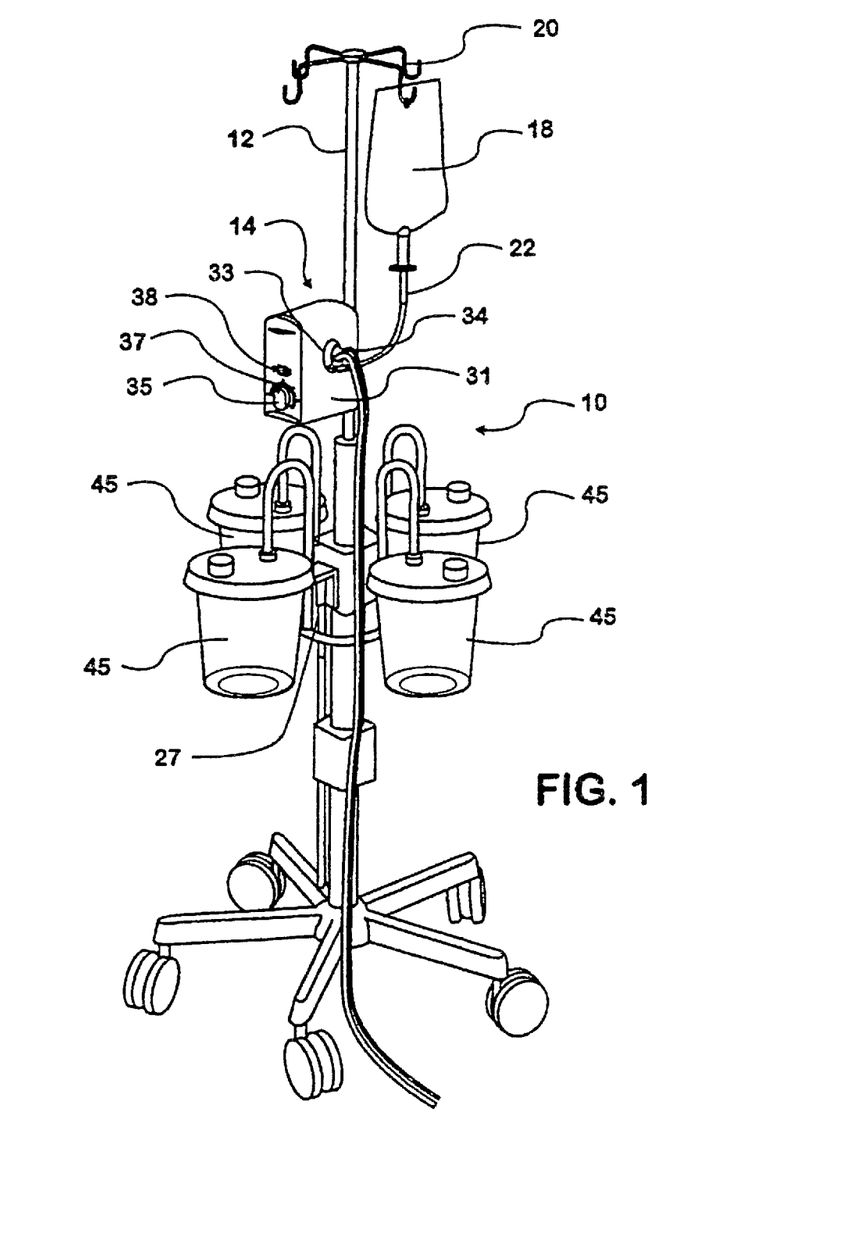
FIG. 1 is a perspective view of a suction irrigation system in accordance with the principles of the present invention seen in its operational environment.

Referring to FIG. 1, a perspective view of a suction irrigation system in accordance with the principles of the present invention seen in its operational environment. The suction irrigation system 10 is contained on a portable support pole 12. The suction irrigation system 10 includes an electronically controlled pump 14. A source of irrigation fluid is provided in fluid communication with the pump 14. In a preferred embodiment, the source of irrigation fluid is a large volume solution bag 18, which is hung from a bag hanger 20 provided on the support pole 12, and is in fluid communication with the pump 14 via an irrigation tube 22.

Figures 11, 12:
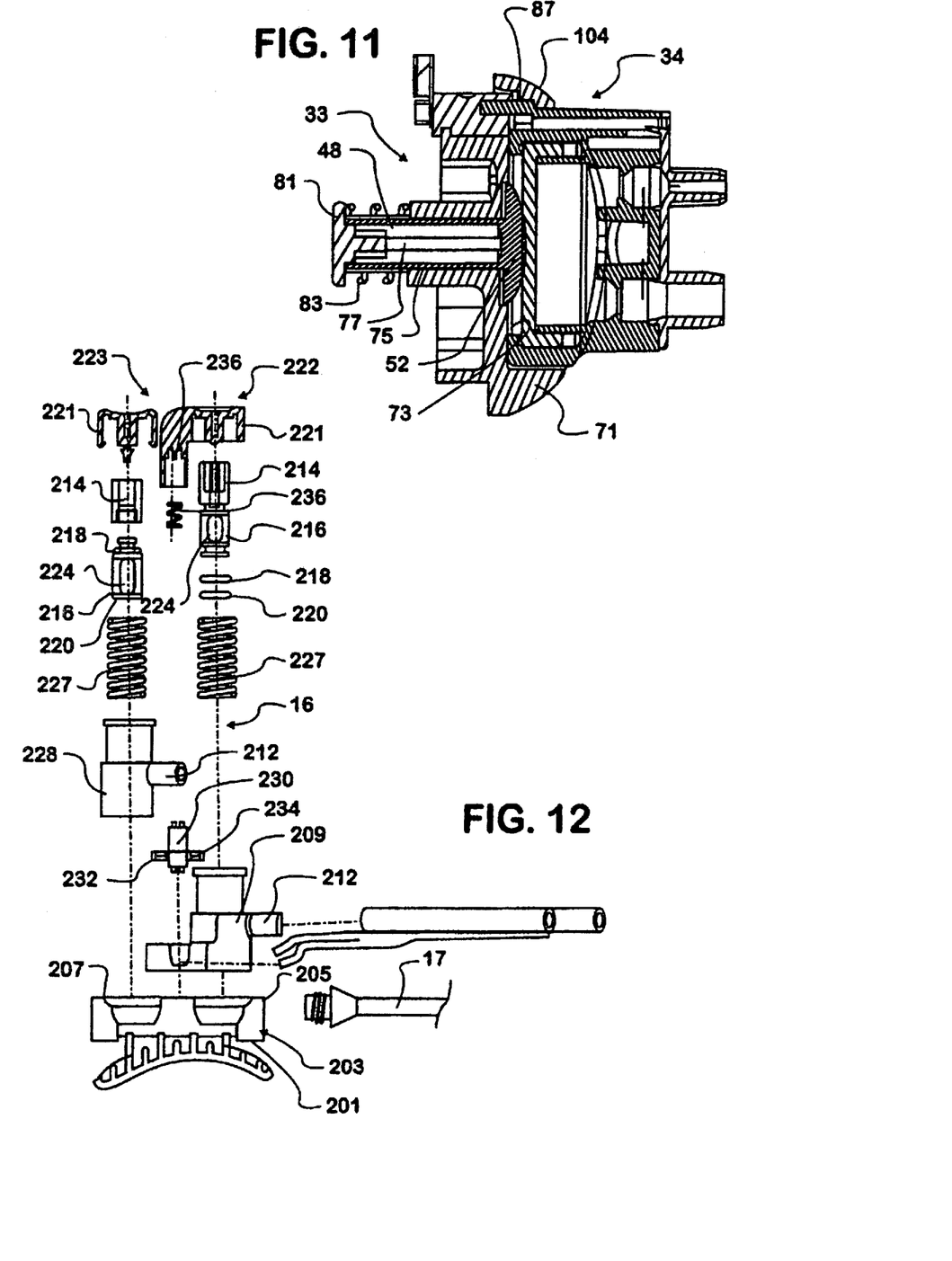
FIG. 11 is a cross-sectional view of the cassette mated in the socket.
FIG. 12 is an exploded view of the suction/irrigation hand piece.

The suction irrigation system 10 also includes a trumpet valve 16 having a suction/irrigation probe 17 (as seen in FIG. 12). A drainage reservoir is in fluid communication with the trumpet valve 16. In a preferred embodiment, the drainage reservoir comprises a plurality of suction canisters 45, which are supported by a canister support 27 provided on the support pole 12, and are in fluid communication with the trumpet valve 16 via a suction tube.

Figure 2A:
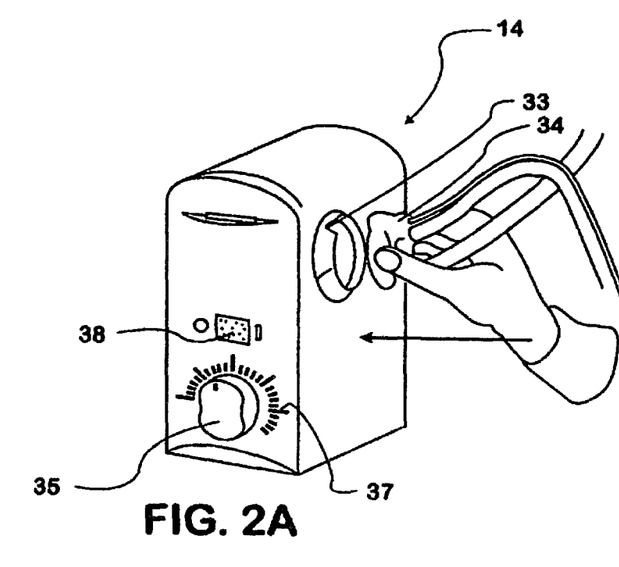
FIGS. 2A and 2B are each detailed perspective views of the pump and cassette of FIG. 1.
Figure 2B:
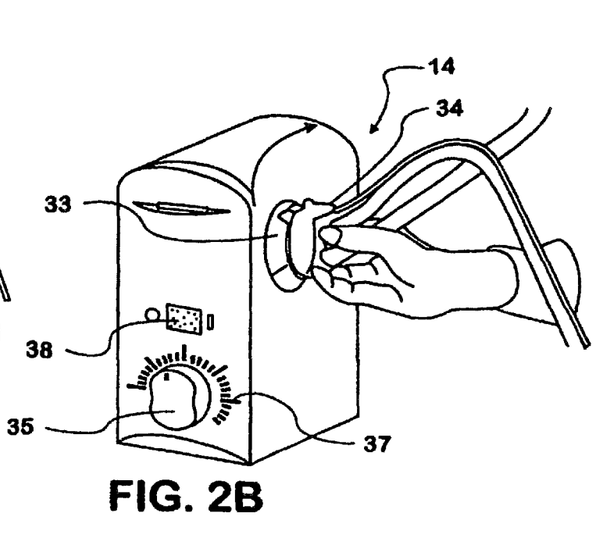

The pump 14 includes a pump body 31, best seen in FIG. 2. The pump body 31 includes a quick connect/disconnect socket 33 thereon adapted to receive a cassette 34. A power on/off switch 38 is provided. The pump body 31 further includes a speed control knob 35 that is used by the health care profession to adjust the speed of the pump 14. A corresponding grid 37 is defined adjacent the speed control knob 35 to provide the health care profession with a visual indication of the pump speed.

The control knob 35 includes a ball plunger (not seen) on the backside that interacts with a ratchet contained on the pump body 31 to provide an audible click and tactile feel when the speed of the pump is changed. A mounting clamp 39 (seen in FIG. 3) is provided in the rear of the pump body 31 to clamp the pump 14 to the support pole 12. Referring back to FIG. 1, the mounting clamp 39 includes pole receiving housing 41 and a threaded clamp 43. An electrical cord is provided that is adapted to be inserted into a standard wall outlet to provide power to the pump 14. The electrical cord is attached to a transformer 44 (seen in FIG. 3) to provide the appropriate power level.

Figure 3:
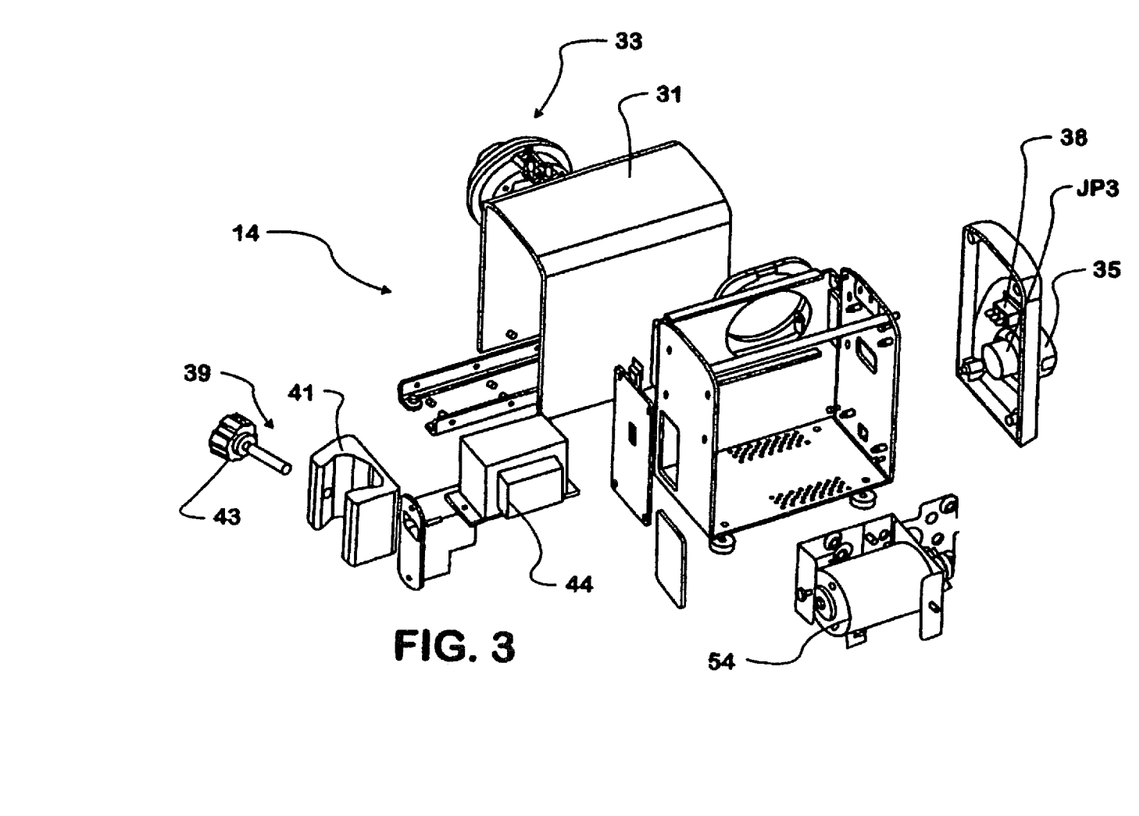
FIG. 3 is an exploded view of the hardware of the pump of FIG. 1.

Referring now to FIG. 3, an exploded view of the hardware of the pump 14 of FIG. 1 is seen. A reciprocally movable pump piston 48 (seen in FIG. 5) is provided in the pump 14. The pump piston 48 is operatively connected to an electric motor 54 disposed in the pump body 31. The electric motor 54 also is electronically connected to the speed control knob 35 by use of a speed control potentiometer JP3. The power on/off switch 38 and the speed control knob 35 are electronically connected to pump control electronics (described below).

Figure 4:
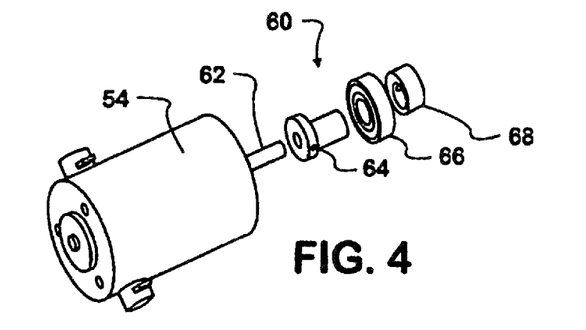
FIG. 4 is a detailed view of the electric motor and the concentric camming mechanism of FIG. 3.

The operative connection between the piston 48 and the electric motor 54 is via a camming mechanism 60 seen in FIG. 4. The electric motor 54 includes a drive shaft 62. The camming mechanism 60 includes eccentric drive shaft 64 that is secured to the drive shaft 62. An eccentric bearing 66 rides on the eccentric drive shaft to impart reciprocal motion to the piston 48. A counter weight 68 is provided to balance the drive shaft 64.

Figure 5:
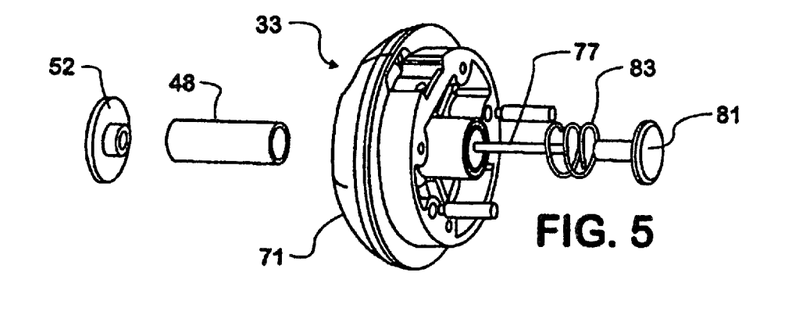
FIG. 5 is an exploded view of the socket of FIG. 3.
Figure 10A:
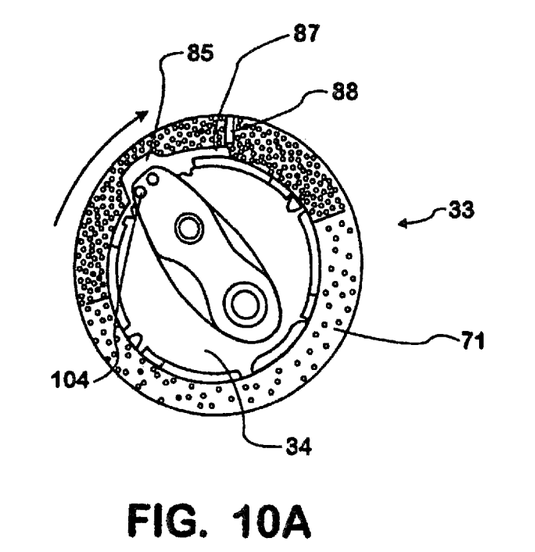
FIGS. 10A and 10B are each detailed views of the cassette grooves and the socket tabs of FIGS. 5 and 6.
Figure 10B:
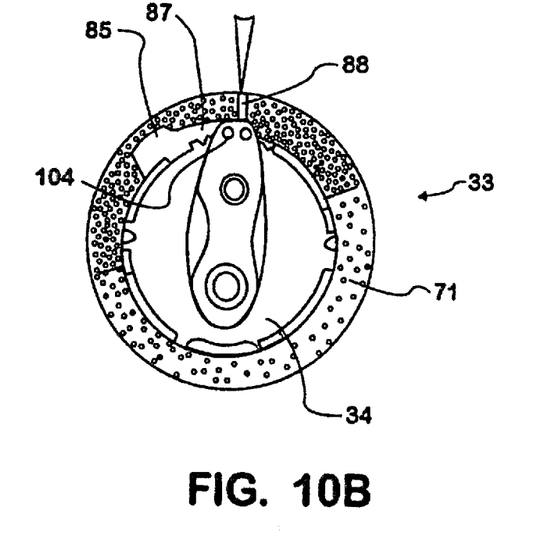

Referring now to FIG. 5, an exploded view of the socket 33 is seen. The socket 33 includes an outwardly extending collar 71. The outwardly extending collar 71 defines a receiving cavity 73 into which the cassette 34 is mated (seen in FIG. 10). A through hole 75 is defined perpendicular to the plane of the receiving cavity 73. The through hole 75 accommodates the pump piston 48. A piston cap 52 is disposed in the receiving cavity 73. The inner periphery of the pump piston 48 includes a piston button 81, which is secured to the piston cap by an extension 77. A piston return spring 83 is secured in a biased position between the piston cap and the piston button 81.

In a preferred embodiment, the socket 33 includes a tab receiving recess connecting with a tab-receiving groove. To provide polarized insertion and guided coupling of the cassette 34 in the socket 33, the cassette 34 includes a cooperating tab, as explained in detail below.

Figure 6:
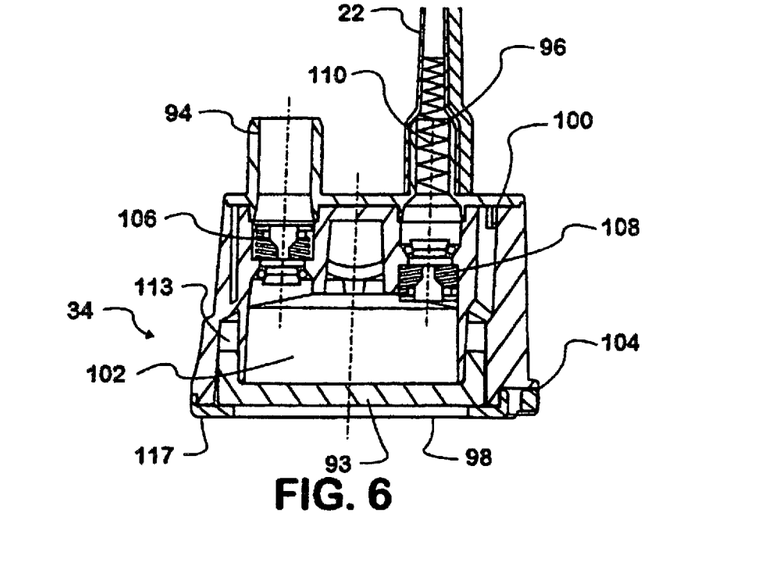
FIG. 6 is a cross sectional, exploded view of the cassette of FIG. 3.

Referring to FIG. 6, a cross sectional view of the cassette 34 is seen. The cassette 34 includes a diaphragm 93, an inlet port 94 for connecting the source of irrigation fluid to the cassette 34, and an outlet port 96 for connecting the cassette 34 to the trumpet valve 16. In order to avoid kinking at the point of contact between the irrigation tube 22 and the outlet port 96, a strain relief spring 110 can be utilized. The inlet port 94 of the cassette 34 is of a larger diameter than the outlet port 96. This is because, when the diameter of the irrigation flow orifice and the diameter of the aspiration suction orifice are the same, the irrigation flow orifice is found to be the restricting element on the through-put of the fluid. Additionally, an access spike is used to penetrate an intravenous solution container access port. The diameter of the access spike is maximized without jeopardizing the ability to connect to a standard intravenous solution container access port.

The cassette 34 further includes a front end 98, an opposed rear end 100, and a fluid flow passageway 102 defined between the inlet port 94 and the outlet port 96. The fluid flow passageway 102 defines a pump chamber. The front end 98 of the cassette 34 can preferably include a laterally outwardly projecting tab 104 that, with the tab-receiving groove 87 (seen in FIG. 10) of the socket 33 provides polarized insertion and coupling of the cassette 34 in the socket 33. A spring biased poppet valve 106 is disposed adjacent the inlet port 94 while a second spring biased poppet valve 108 is disposed adjacent the outlet port 96. The poppet valves 106, 108 provide reliable responsive opening and closing of the fluid flow passageway openings to provide large volume irrigation flow through the cassette 34 while requiring a small load to open the poppet valves 106, 108 to allow flow to flow through.

Figure 7:
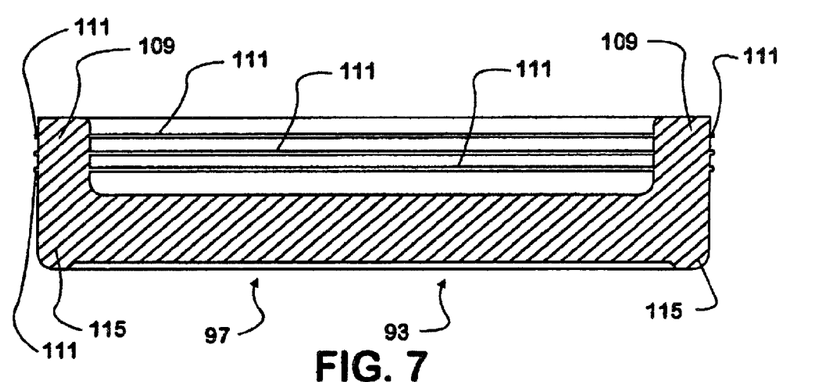
FIG. 7 is a cross sectional view of the diaphragm of FIG. 6.

Referring now to FIG. 7, a cross sectional view of a resilient displaceable diaphragm 93 is seen. The diaphragm defines an inner portion that faces the pump chamber of the cassette and an outer portion that interacts with the pump piston. Additionally, the diaphragm 93 is concave shaped on the inside or fluid chamber side. This helps to direct the fluid through the chamber to avoid fluid turbulence in the pump chamber during pumping action.

In diaphragm designs of the prior art, a major concern is its ability to follow the piston while improving the return stroke. The inventive diaphragm 93 of the present invention includes a graduated cross-sectional thickness dimension such that the thickness dimension increases from a central portion of the diaphragm 93 to radially outward portions of the diaphragm 93. This provides a higher stiffness as the outside of the diaphragm 93 is approached as compared to the middle portion of the diaphragm 93. The durometer of the diaphragm 93 also is important as the diaphragm 93 interacts with the spring 83 carried on the reciprocating piston 48 of the collar 71. The force of the spring 83 must be sufficient, combined with the durometer of the diaphragm 93 to allow a significant enough pumping cycle to gain the required flow.

In addition, the stiffness and durometer of the diaphragm is also varied to balance the return stroke efficiency with pump power required to drive the system. The diaphragm 93 is considerably larger in diameter then the piston cap. This allows the outer parameter of the diaphragm 93 to act as a "hinge" or "bellows" mechanism to allow the reciprocating movement of the diaphragm 93. The diaphragm acts like a hinge, balancing both cross-section dimension and durometer to facilitate the return mechanism Alternatively, the cross section of the diaphragm can be modeled more like a cantilever than a hinge to achieve a more effective return mechanism.

Figure 8:
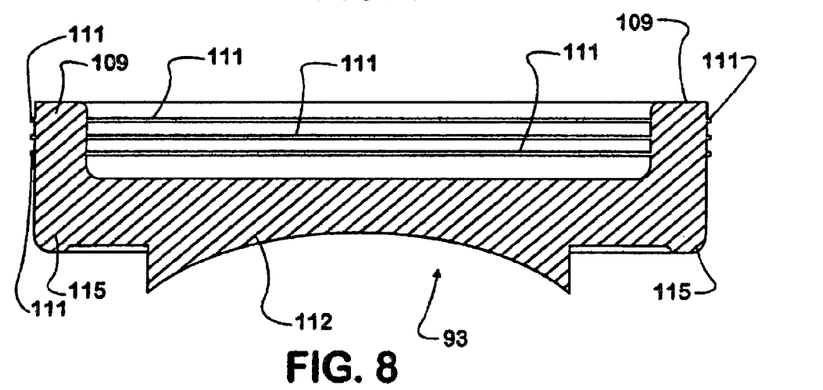
FIG. 8 is a cross-sectional view of an alternative embodiment of the diaphragm.

Alternative embodiments of the diaphragm are also contemplated as within the scope of the present invention. FIG. 8 shows a cross-sectional view of an alternative embodiment of the diaphragm. This alternative embodiment has two features. First, the diaphragm defines a cup-like portion 112 designed to interact with the piston. The radius of the cup is smaller than that of the piston, thereby creating a suction cup like mechanism. In addition, since the cross section already conforms to the piston, the motion of the diaphragm during the piston forward stroke, is more efficient.

Figure 9:
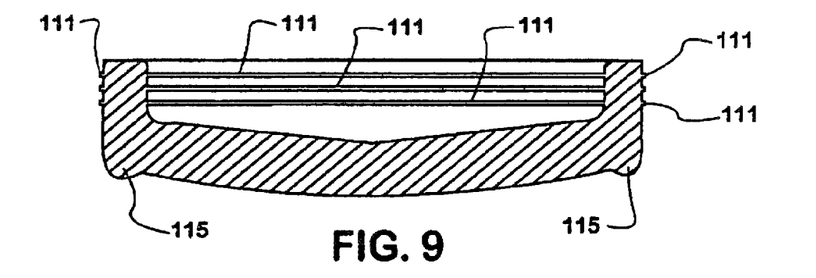
FIG. 9 is a cross-sectional view of an alternative embodiment of the diaphragm.

Alternatively, a dome can be defined which is protruding in opposite direction to pump piston. FIG. 9 shows a cross-sectional view of this alternative embodiment of the diaphragm. Once the piston has moved forward fully, given the cross-section, the "oil-can" geometry will cause the dome to have a greater tendency to return to its rest position thereby following the piston more effectively. In all alternative embodiments, the durometer was also varied to balance the return stroke efficiency with pump power required to drive the system.

The resilient displaceable diaphragm 93 is mounted in the cassette 34. The diaphragm 93 is preferably secured in the cassette 34 by use of two securing methods. Initially, the diaphragm 93 is formed with a downwardly extending portion 109 on the outer periphery. The diaphragm 93 includes on the downwardly extending portion 109 a series of ridges 111 that act to further secure and seal the diaphragm 93 into a fluid type engagement. This downwardly extended portion 109 is friction fit into a groove 113 (seen in FIG. 6) defined in the cassette 34.

On the outside of the outer periphery of the diaphragm 93, an outwardly extending bulb portion 115 is provided. This bulb portion 115 acts in conjunction with a retaining ring 117 (seen in FIG. 6) that is used to secure the diaphragm 93 into the cassette 34. When the retaining ring 117 is engaged, the retaining ring 117 pushes on the bulb portion 115, which causes the downwardly extending portion 109 of the diaphragm 93 in the groove 113 to expand outwardly, thus helping to secure the diaphragm 93 it into position. The cassette 34, the diaphragm 93 and retaining ring 117 preferably can be sonic welded together in a fluid tight engagement.

In a preferred embodiment, the front end of the cassette 34 includes a laterally outward projecting tab 104 and the socket 33 includes a tab receiving recess 85 connecting with a tab receiving groove 87 to provide polarized insertion and guided coupling of the cassette 34 in the socket 33. This is seen in FIG. 10.

The groove 87 engagement provides a two phased camming mechanism. In the first portion, the cassette 34 is pulled towards the plunger of the receiving cavity 73 to insure the proper orientation. In the second portion, the cam includes a plain member that is used to insure that the cassette 34 is not "jiggled" out of position during use. Additionally, the tabs are preferably designed on the collar 71 while the grooves 87 are preferably designed on the cassette 34. Because in the preferred embodiment the collar 71 is metal while the cassette 34 is plastic, placement of the tabs on the collar 71 and the groove 87s on the cassette 34 helps insure structural integrity given the forces that under which the tabs are placed.

Additionally, the tab in groove 87 arrangement between the cassette 34 and the socket 33 allows only a single engagement orientation of the socket 33 and the cassette 34. This insures that the socket 33 and the cassette 34 are in the proper orientation for pumping action. The proper orientation of the cassette 34 and pump 14 is further confirmed to the user by use of an indicator line 88 on the collar 71 that aligns with the tab 104 when the cassette 34 is secured in the proper position. In addition, as explained below an audible click is generated when the cassette 34 is secured in the proper position.

Referring to FIGS. 2 and 10, installation of the cassette 34 in the socket 33 is seen. Initially, in FIG. 2A, the health care professional aligns the cassette 34 with the socket 33. The tab 104 on the cassette 34 is aligned with the tab receiving recess 85 of the socket 33, as seen in FIG. 10A. The health care professional then turns the cassette 34 in the socket 33, as seen in FIG. 2B. This guides the tab 114 of the cassette 34 in the tab-receiving groove 87 of the socket 33, as seen in FIG. 10B. The indicator line 88 on the collar 71 aligns with the tab 104 when the cassette 34 is secured in the proper position.

Referring now to FIG. 11, a cross-sectional view of the cassette 34 mated in the socket 33 is seen. The front end of the cassette 34 is designed such that it is releasably received in the socket 33 and movable to a mated and locked position. This disposes the piston 48 in contact with the diaphragm 93. The front end further including a second mateable electrical contact disposed to make mated electrical contact with the first mateable electrical contact when the front end is moved to the locked position in the socket 33. The second mateable electrical contact is electrically connected to a switch operatively associated with the suction/irrigation probe 17. Like the first mateable electrical contacts, the second mateable electrical contacts can comprise an insulation displacement contact.

In an embodiment, the electrical contacts comprise ball plunger on the pump socket 33 and insulation displacement contacts on the cartridge cassette 34. The electrical contacts are located in the mating interface between the front end of the cartridge cassette 34 and the pump socket 33 at a generally splash free location. In an embodiment, the pair of wire leads extends between the switch housing on the trumpet valve 16 and the second electrical contact in the front end of the cassette 34. The irrigation fluid tubing and the suction tubing may all be co-extruded using quadruple extrusion methods whereby two tubes and two wires are extruded together and connected in an adhering manner. The wire leads are preferably stranded wires to minimize adverse effects on drapeability of the tubing. Preferably, the tubing will be provided with a frosted finish to reduce sticking behavior.

The cassette electrical contacts are manufactured by initially threading the contact wires through a groove defined in the cassette 34. The cassette electrical contacts are then secured into the housing. The cassette electrical contacts include a wire insert to enable electrical contact between the wiring and the electrical contacts. This avoids both a soldering step or a crimping step in the manufacturing process. In addition, the wire aperture includes a one-way "fish scale" tab which allows the wire to be inserted into the cassette 34 but secures the wire from being pulled out of the cassette 34. Housing for the contacts includes a plastic bridge that defines two apertures into which the bulb contacts fit to enable an electrical contact. The cassette housing includes a tab that is designed to prevent the cassette electrical contacts from backing out.

In a preferred embodiment, in addition to the insulation displacement electrical contact, the collar 71 includes two additional ball plungers. The insulation displacement electrical contact acts as a single leg of the three-leg ball plunger system. The three leg plungers serve two principal purposes. First, they help to secure the cassette 34 in the receiving cavity 73 in a manner so that when the cassette 34 and collar 71 are in operation, the cassette 34 is held firmly in the receiving cavity 73 without "jittering." Second, the ball plungers provide a tactile "click" engagement with a cassette 34 when the cassette 34 is loaded into the proper position to give the user the indication that the cassette 34 has been secured. This assures proper orientation of the cassette 34 in the receiving cavity 73.

When the cartridge cassette 34 is in its mated and locked position in the socket 33, depression of the irrigation valve closes the switch on the trumpet valve 16, causing the electronic pump control circuit to turn the pump 14 on. The pump pumps irrigation fluid in a pulsed manner from the source of irrigation fluid, through the cassette 34 and through the trumpet valve 16 to a discharge opening in the suction/irrigation probe 17. Thus, the pumping system provides a pulsating pumping parameter to the site of the operation. The pulsating pumping action generates a "water pic" like pulsating action at the surgical site, which helps to flush out the site. In the mated and locked position of the cassette 34 in the socket 33, and with the pump piston 48 in a fully retracted position with respect to the cassette 34, a front end on the pump piston 48 contacts the diaphragm 93 and presses against the diaphragm 93 to preload the diaphragm 93 into a stressed position. This helps to avoid diaphragm float during the reciprocating pumping cycle.

Referring now to FIG. 12, an exploded view of the trumpet valve 16 is seen. The trumpet valve 16 includes a trumpet valve housing 201 comprising a conduit 203 having an axial bore extending from a first end 205 to an opposed second end 207.

The trumpet valve defines an irrigation fluid valve 222 and a suction valve 223. With respect to the irrigation fluid valve 222, a hollow cylindrical barrel 209 projects from the valve housing 201 at a point intermediate the first end 205 and the second end 207. The barrel 209 includes a central valve passage extending therethrough to an opposed opening communicating with the axial bore 203. The barrel 209 further includes a port projection 212 extending outwardly from the barrel 209. A valve stem 214 including a slider portion 216 with first and second spaced apart sealing members 218, 220 are slidably and sealably disposed in the central valve passage. An actuator cap 221 is secured to the cylindrical valve stem 214.

The valve stem 214 includes a valve aperture 224 extending through the slider portion 116 between the first sealing member 218 and the second sealing member 220. The valve stem 214 is reciprocally movable within the barrel 209 between a normally closed, released position and a pressed, open position. In the normally closed, released position the valve stem 214 is displaced away from the barrel 209 by a spring 227, with the first and second sealing members 218, 220 sealingly disposed in the valve passage on opposed sides of the port projection 212. In the pressed, open position the valve stem 114 is moved inwardly within the barrel 209 so that the valve aperture 224 on the slider portion 216 is positioned to define a continuous fluid flow path extending from the port projection 212, along the valve aperture 224 to the axial bore.

The suction valve 223 is also defined on the trumpet valve 16. A second hollow cylindrical barrel 228 projects from the valve housing 201 at a point intermediate the first end 205 and the second end 207. The second hollow cylindrical barrel 228 includes like elements to the first hollow cylindrical barrel 209, which are designated in FIG. 12 with like reference numbers, defining a suction circuit connectable to a source of vacuum. Depressing the irrigation valve 222 opens an irrigation line to the axial bore for providing irrigation fluids to a surgical site through the suction/irrigation probe 17. Depressing the suction valve 223 opens a vacuum line to the axial bore for removal by suction of irrigation and body fluids from a surgical site through the suction/irrigation probe 17.

The valve housing includes switch-housing 230 having a pair of switch contacts 232, 234 adjacent the irrigation fluid valve 222. A spring 236 is mounted on the irrigation fluid valve 222 and positioned to electrically contact each of the switch contacts 232, 234 when irrigation fluid valve 222 is moved to a depressed, "on" position.

The pump 14 has a variable flow rate mechanism that enables the user to vary the flow rate of the fluid. In order to reduce the likelihood of the pump 14 creating an over pressurized situation, two aspects are provided with the pump 14. Initially, the electric motor 54 is designed so that if a predetermined load occurs, the pump 14 shuts off. Additionally, the pump 14 includes a thermal shut off so that if the pump 14 is running unimpeded, the pump 14 will shut off prior to burning itself out, as described in detail below.

Figure 13:
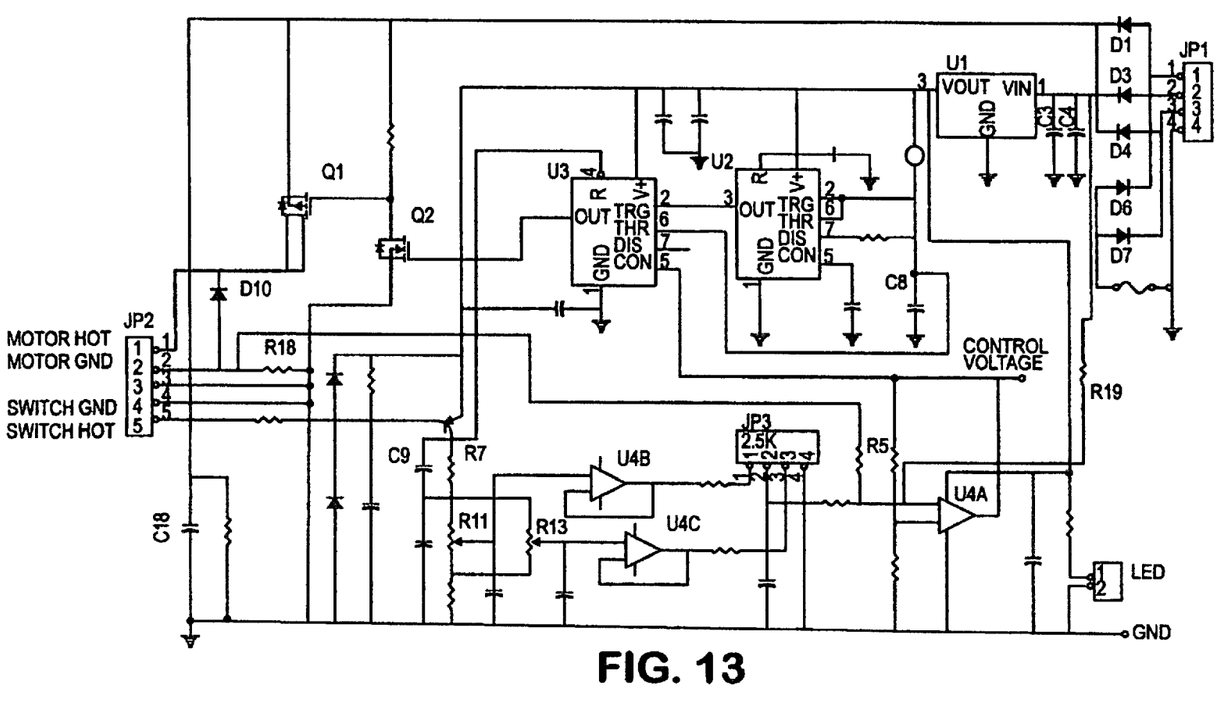
FIG. 13 is a schematic of the electronic control circuitry.

Referring now to FIG. 13, a schematic of the electronic control circuitry is seen. Power is supplied from a standard electric wall outlet to a power entrance module with an integrated medical-rated alternative current (AC) line filter, a power transformer and power supply electronic components. The power supply electronic components are described below.

Two isolated winding from the transformer are connected to the electronics controller. Voltage from the first winding is half-wave rectified by diode D3, filtered into direct current (DC) by capacitors C3, C4, then converted to the electronics controller logic voltage by voltage regulator U1.

Voltage from the second winding is rectified by diodes D1, D4, D6, D7 and filtered by capacitor C11 to provide electric motor 54 power. To reduce sensitivity to variations in line voltage, a feedback voltage is sent through resistor R19 to the input line of a speed control operational amplifier circuitry.

The speed control operational amplifier circuitry consists of three operational amplifiers U4A, U4B, U4C. The feedback voltage is sent through resistor R19 to the input line of operational amplifier U4A.

An electronics controller is provided. The electronics controller is comprised of pulse width modulation (PWM) oscillator U2, PWM oscillator U3, the operational amplifier circuitry, including operational amplifiers U4A, U4B, U4C, and transistor Q2. The width of the pulses generated by PWM oscillator U2 is modulated by PWM oscillator U3 then sent to the motor control switching transistor Q1.

If the duty cycle of the pulses are zero, the electric motor 54 is turned off. If the duty cycle of the pulses is at the maximum length, the electric motor 54 runs at full speed. Any pulse width between these two values operates the electric motor 54 at a speed between full on and full off. The operational amplifier circuitry is used to buffer the speed control potentiometer JP3. Transistor Q2 is used as the start switch control amplifier.

Two outputs are derived from the PWM oscillator U2. One output is used to reset the PWM oscillator U3 at the beginning of each pulse cycle. A second output, taken from across capacitor C8, is a linear-ramp sawtooth voltage, which starts at zero volts at the beginning of a pulse cycle, and ramps up to a percentage of the full voltage range at the end of the cycle.

Because the waveform taken at capacitor C8 is linear with respect to voltage and time, the instantaneous voltage actually represents the amount of time since the pulse began. The PWM oscillator U3 compares the voltage output from the speed control potentiometer JP3 to the instantaneous voltage of the linear-ramp sawtooth voltage, and turns off power to the electric motor 54 any time that the linear-ramp sawtooth voltage is higher than the speed control potentiometer JP3, until the start of the next pulse cycle.

As previously described, the electric motor 54 is started by a switch located on the trumpet valve 16. When this valve is opened, the switch contacts within the valve close, which grounds a signal line that ultimately starts the pump. This is accomplished by the trumpet valve switch interface, described below.

The input from the switch comes in on connector JP2. When grounded, this signal turns on transistor Q2, which in turn provides an excitation voltage to the speed-control potentiometer JP3. The motor speed control range operable by the speed-control potentiometer JP3 is set by adjusting resistors R11 and R13. In operation, resistor R11 sets the maximum possible speed and resistor R13 sets the minimum speed of the electric motor 54.

Capacitor C9, connected across resistor R7, is normally discharged until the trumpet valve switch is closed. When the switch is closed, the electric motor 54 is given a short starting current boost until capacitor C9 is charged. When capacitor C9 is charged, the electric motor 54 current drops to the nominal setting dictated by the speed-control potentiometer JP3. At normal speed settings capacitor C9 has little effect; at lower speed settings, however, capacitor C9 ensures reliable motor starting.

The output of the speed-control potentiometer JP3 is fed to operational amplifier U4A. Operational amplifier U4A buffers the signal and presents it to PWM oscillator U3. A current feedback resistor R5 stabilizes the loop for low speed torque requirements. This is accomplished by placing a current sensing resistor R18 in the motor drive circuit. A voltage is then generated across resistor R5 that is summed up with the speed control potentiometer JP3 to create a variation in the speed set value in proportion to the current being driven through the electric motor 54.

The electric motor 54 is connected between the power supply, transistor Q1, and ground. Reverse voltage protection for transistor Q1 is provided by diode D10. When the gate input to transistor Q1 is high, the electric motor 54 runs; when it is zero, the electric motor 54 coasts to a stop.

Thus, the present invention provides a new and improved disposable trumpet valve tube cassette assembly, as well as, a new and improved surgical irrigation apparatus generally comprising a disposable trumpet valve tube cassette assembly and a modified and improved electronically controlled pump and control circuitry. The present invention provides a suction irrigation system which place direct irrigation flow under the one handed control of the surgeon. The present invention further provides a disposable suction irrigation cassette assembly that capable of operating with a pump in a manner which delivers consistently controlled irrigation fluid volumes, at controlled rates and pressures under the control of the surgeon. The present invention provides a suction irrigation system that is able to deliver, on demand, consistent and accurate quantities of irrigation fluid in a non-distracting manner under control of the surgeon. The present invention provides control circuitry so that the pump will shut off prior to burning itself out.

It should be understood that various changes and modifications to the preferred embodiment described herein will be apparent to those skilled in the art. Such changes and modifications can be made without departing from the spirit and scope of the present invention and without demising its attendant advantages. It is therefore intended that such changes and modifications be covered by the appended claims.

What is claimed is:

1. A surgical irrigation pump for use with a cassette having a pumping chamber, the pump comprising:
    a socket disposed on a pump housing, the socket removably receiving the cartridge cassette to establish working communication between a pump actuator provided in the socket and the pumping chamber;
    a motor that operates the pump actuator; and
    an irrigation valve comprising an actuator member and a switch, the switch activatable by depression of the actuator member, wherein activation of the switch causes the motor to operate the pump actuator.

2. The surgical irrigation pump of claim 1, wherein the pump pumps irrigation fluid in a pulsed manner.

3. The surgical irrigation pump of claim 1, wherein the socket is in juxtaposition to the pump actuator.

4. The surgical irrigation pump of claim 1, wherein the cartridge cassette includes a laterally outwardly projecting tab and the socket includes a tab-receiving recess connected with a tab-receiving groove to provide coupling of the cartridge cassette in the socket.

5. The surgical irrigation pump of claim 1, further comprising a means for allowing a removable quick-lock engagement between the pump housing and the cartridge cassette.

6. The surgical irrigation pump of claim 5, wherein the means for allowing a removable quick-lock engagement includes a laterally outwardly projecting tab and the socket includes a tab-receiving recess connected with a tab-receiving groove to provide coupling of the cartridge cassette in the socket.

7. The surgical irrigation pump of claim 1, further comprising an electronic pump control circuit that selectively controls pumping operations of the pump in response to a signal received from the switch.

8. The surgical irrigation pump of claim 7, wherein the electronic pump control circuit includes a controller having a pulse generator that generates pulses.

9. The surgical irrigation pump of claim 8, wherein a duty cycle of the generated pulses controls a speed of the motor.

10. The surgical irrigation pump of claim 1, wherein the socket is in juxtaposition to the pump actuator such that, in a mated position of the cartridge cassette in the socket, the pump actuator preloads the pumping chamber.

11. A surgical irrigation pump for use with a cassette having a pumping chamber, the pump comprising:
    a socket disposed on a pump housing, the socket removably receiving the cartridge cassette to establish working communication between a pump actuator provided in the socket and the pumping chamber;
    a motor that operates the pump actuator, the motor powered by a power supply external to the cartridge cassette;
    an irrigation valve comprising an actuator member and a switch, the switch activatable by depression of the actuator member; and
    an electronic pump control circuit that selectively controls pumping operations of the pump in response to activation of the switch.

12. The surgical irrigation pump of claim 11, wherein the socket is in juxtaposition to the pump actuator.

13. The surgical irrigation pump of claim 11, wherein the cartridge cassette includes a laterally outwardly projecting tab and the socket includes a tab-receiving recess connected with a tab-receiving groove to provide coupling of the cartridge cassette in the socket.

14. The surgical irrigation pump of claim 11, further comprising a means for allowing a removable quick-lock engagement between the pump housing and the cartridge cassette.

15. The surgical irrigation pump of claim 14, wherein the means for allowing a removable quick-lock engagement includes a laterally outwardly projecting tab and the socket includes a tab-receiving recess connected with a tab-receiving groove to provide coupling of the cartridge cassette in the socket.

16. The surgical irrigation pump of claim 11, wherein the electronic pump control circuit includes a controller having a pulse generator that generates pulses.

17. The surgical irrigation pump of claim 16, wherein a duty cycle of the generated pulses controls a speed of the motor.

18. The surgical irrigation pump of claim 11, wherein the socket is in juxtaposition to the pump actuator such that, in a mated position of the cartridge cassette in the socket, the pump actuator preloads the pumping chamber.

19. The surgical irrigation pump of claim 11, wherein the pump pumps irrigation fluid in a pulsed manner.

* * * * *